(12) United States Patent
Hitomi et al.

(10) Patent No.: US 7,820,211 B2
(45) Date of Patent: Oct. 26, 2010

(54) COSMETIC MATERIAL CONTAINING SWEET PEA EXTRACT

(75) Inventors: Takamasa Hitomi, Yokohama (JP); Shoko Matsukuma, Yokohama (JP)

(73) Assignee: Fancl Corporation, Kanagawa (JP)

( * ) Notice: Subject to any disclaimer, the term of this patent is extended or adjusted under 35 U.S.C. 154(b) by 274 days.

(21) Appl. No.: 11/910,237

(22) PCT Filed: Mar. 14, 2006

(86) PCT No.: PCT/JP2006/304966

§ 371 (c)(1),
(2), (4) Date: Oct. 30, 2007

(87) PCT Pub. No.: WO2006/112224

PCT Pub. Date: Oct. 26, 2006

(65) Prior Publication Data

US 2009/0061030 A1    Mar. 5, 2009

(30) Foreign Application Priority Data

Apr. 1, 2005    (JP) ............................. 2005-106563

(51) Int. Cl.
  *A61K 36/00*    (2006.01)
  *A61K 9/00*    (2006.01)
  *A61K 47/00*    (2006.01)
  *A61K 36/48*    (2006.01)

(52) U.S. Cl. ........................ 424/757; 424/425; 424/400; 424/439

(58) Field of Classification Search ........................ None
See application file for complete search history.

(56) References Cited

U.S. PATENT DOCUMENTS 6,861,077 B1 *   3/2005   Cannell et al. .............. 424/725

FOREIGN PATENT DOCUMENTS

| EP | 0 532 465 B1 | 9/1992 |
|---|---|---|
| GB | 2093696 A | 9/1982 |
| JP | 57-209209 | 12/1982 |
| JP | 11-315007 | 11/1999 |
| JP | 2001-039852 | 2/2001 |
| JP | 2001-233747 | 8/2001 |
| JP | 2002-128653 | 5/2002 |
| JP | 2004-018793 | 1/2004 |
| JP | 2004-035440 | 2/2004 |
| JP | 2004-043420 | 2/2004 |
| JP | 2004-083432 | 3/2004 |
| JP | 2004-244382 | 9/2004 |
| WO | WO 99/48456 | 9/1999 |
| WO | WO 00/59462 | 10/2000 |
| WO | WO 03/059368 A1 | 7/2003 |

OTHER PUBLICATIONS

Cooney-Curran ("Making Peace in the US: New skin-care anti/aging products direct from spain (Brief Article)." Global Cosmetic Industry. Mar. 2000 vol. 166, No. 3 p. 66, a newsletter article).*

A full translation of Japanese Patent Publication No. JP-2001-233747, Aug. 28, 2001.

* cited by examiner

*Primary Examiner*—Christopher R Tate
*Assistant Examiner*—Randall Winston
(74) *Attorney, Agent, or Firm*—Knobbe Martens Olson & Bear LLP

(57) ABSTRACT

A cosmetic material, cell growth promoting agent, elastase activity inhibiting agent and anti-aging agent containing sweet pea extract, formulated with the aim of preventing or slowing aging.

4 Claims, 2 Drawing Sheets

[Fig. 1]
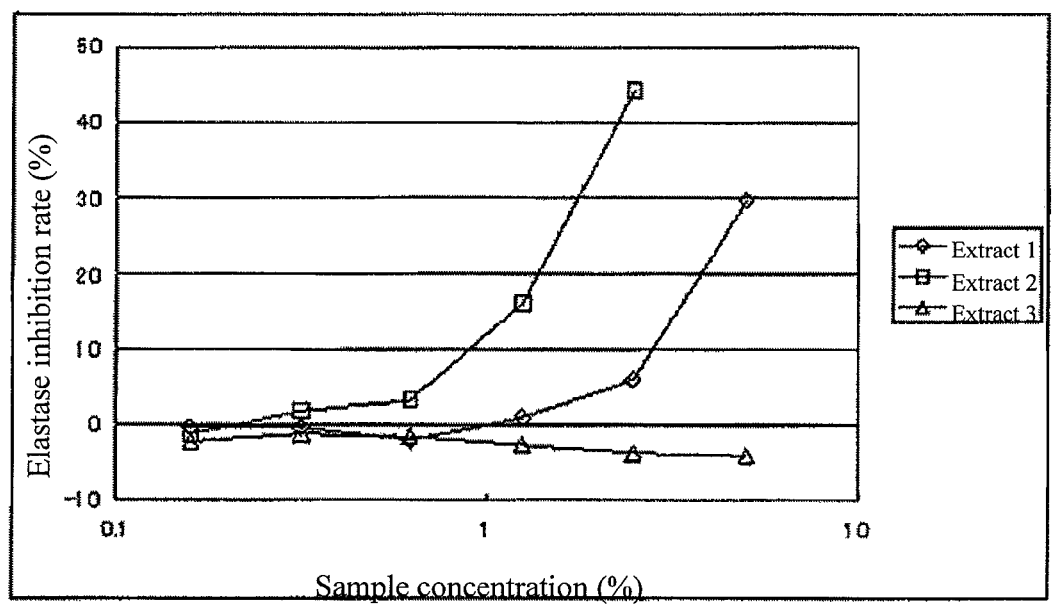
[Fig. 2]
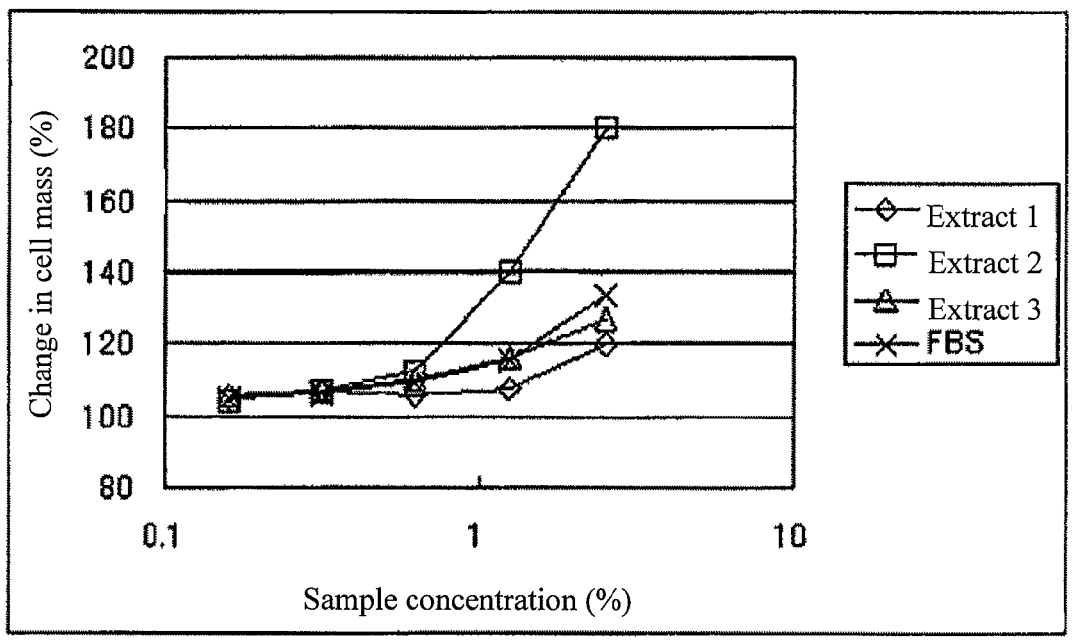

[Fig. 3]
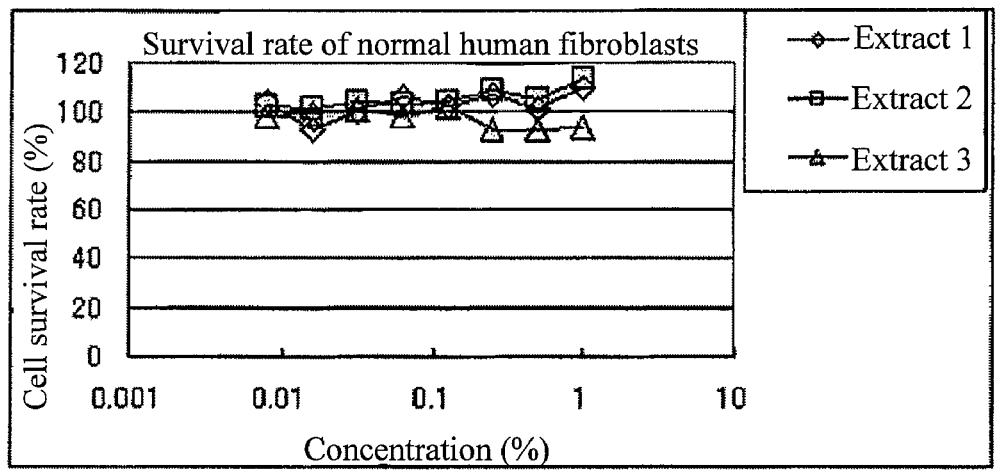
[Fig. 4]
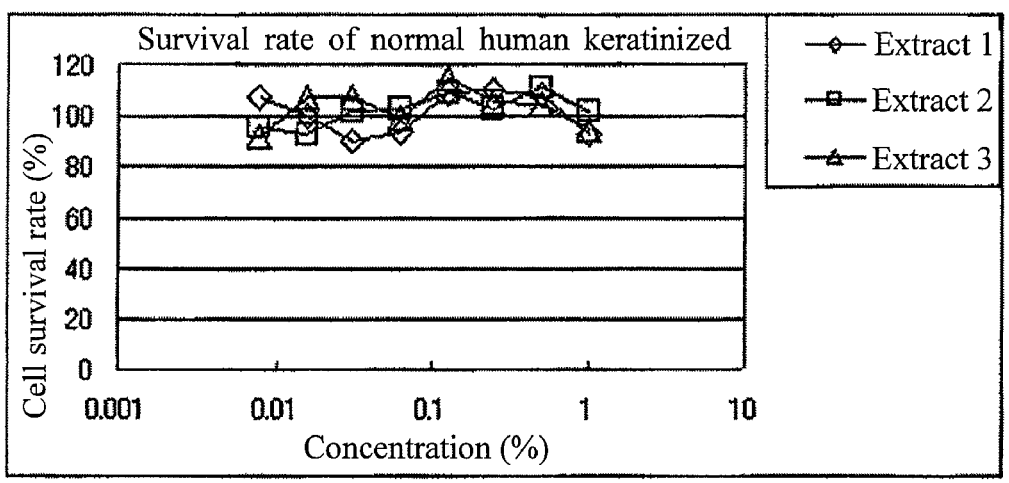
[Fig. 5]
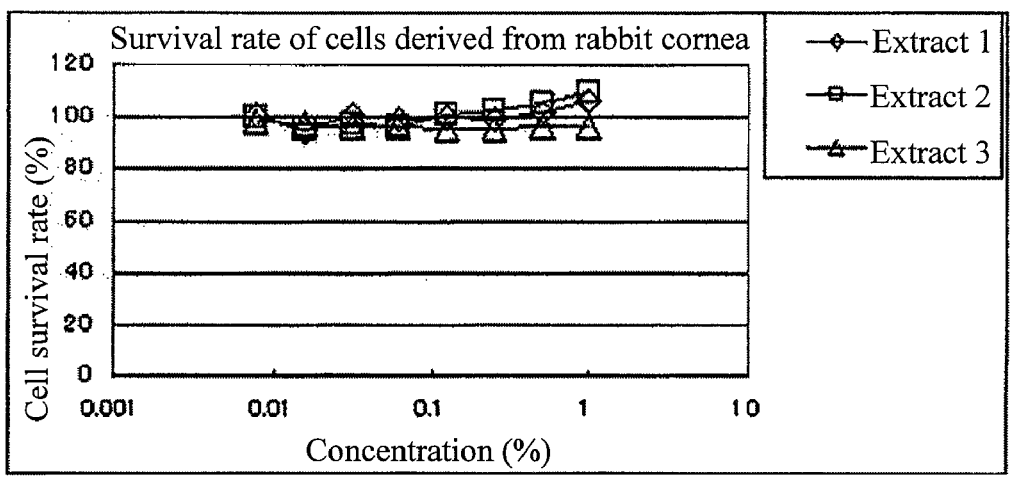

COSMETIC MATERIAL CONTAINING SWEET PEA EXTRACT

This application is the U.S. National Phase under 35 U.S.C. §371 of International Application PCT/JP2006/304966, filed Mar. 14, 2006, which claims priority to Japanese Patent Application No. 2005-106563, filed Apr. 1, 2005. The International Application was not published under PCT Article 21(2) in English.

TECHNICAL FIELD

The present invention relates to a cosmetic material, etc., containing sweet pea extract.

PRIOR ART

As the skin ages, activity and growth of skin cells slow and productions of elastin, collagen, mucopolysaccharides and other extracellular matrixes decrease. Also, decomposition of elastin and collagen is promoted by elastase and collagenase, resulting in wrinkles and sagging skin. Numerous studies have been conducted with the aim of preventing or slowing skin aging, through which a number of components that inhibit elastase activity are known, including *Epipactis helleborine, Neottia nidusavis* var. *mandshurica, Cephalanthera falcate, Orchis aristata* (refer to Patent Literature 1, for example), lychee seed (refer to patent Literature 2, for example), glucosamine (refer to Patent Literature 3, for example), *Agave americana, Agave sisalana* and *Adenophora triphylla* var. *japonica* (refer to Patent Literature 4, for example). Also, aloe vela, almond, sesame, *dioscoreae rhizome*, dandelion, *sambucus nigra, cnidium rhizome, mulberry bark, peach kernel, houttuynia cordata, pholiota nameko, ophiopogon tuber, hibiscus syriacus, coix* seed and *chlorella* (refer to Patent Literature 5, for example) are known, among others, as components that promote the growth of fibroblasts. However, any cosmetic material containing sweet pea extract, nor the property of such cosmetic material to prevent or slow aging, has not heretofore been known.

Patent Literature 1: Japanese Patent Laid-open No. 2004-018793
Patent Literature 2: Japanese Patent Laid-open No. 2004-043420
Patent Literature 3: Japanese Patent Laid-open No. 2004-083432
Patent Literature 4: Japanese Patent Laid-open No. 2004-244382
Patent Literature 5: Japanese Patent Laid-open No. 2004-035440

SUMMARY OF THE INVENTION

Problems to be Solved by the Invention

The present invention provides a cosmetic material having the effect of preventing and slowing aging.

Means for Solving the Problems

The key constitutions of the present invention are summarized below:
1. A cosmetic material comprising a sweet pea extract.
2. The cosmetic material according to 1, wherein a part from which the sweet pea extract is obtained is the flower and/or stem.
3. The cosmetic material according to 1 or 2, characterized in that the sweet pea extract is an extract with water and/or water-soluble organic solvent.
4. A cell growth promoting agent containing an extract from the sweet pea flower and/or stem.
5. An elastase activity inhibiting agent containing an extract from the sweet pea flower.
6. An anti-aging agent whose active ingredient is a sweet pea extract.
7. The anti-aging agent according to 6, wherein a part from which the sweet pea extract is obtained is the flower and/or stem.
8. A cosmetic material comprising the agent described in any one of 4 through 7.

Effects of the Invention

Sweet pea extract has been confirmed to provide the effects of promoting cell growth, inhibiting elastase activity and demonstrating anti-aging property, among others, and therefore a cosmetic material, cell growth promoting agent, elastase activity inhibiting agent or anti-aging agent can be provided that demonstrates each of the aforementioned properties. It has also been confirmed that all of the above substances are very safe.

BRIEF DESCRIPTION OF THE DRAWINGS

FIG. 1 Graph showing the results of elastase activity inhibition test.
FIG. 2 Graph showing the results of cell growth promotion test.
FIG. 3 Graph showing the results of cell toxicity test using normal human fibroblasts.
FIG. 4 Graph showing the results of cell toxicity test using normal human keratinized cells.
FIG. 5 Graph showing the results of cell toxicity test using cells derived from rabbit cornea.

BEST MODE FOR CARRYING OUT THE INVENTION

Sweet pea (*Lathyrus odoratus* L.) is a plant in the genus *Lathyrus* in the family Leguminosae, and is also known as "jako renriso" or "jako endo" in Japanese. It is a horticultural species that grows in the Mediterranean and is mainly used as an ornamental plant. Sweet pea flowers come in various colors including white, pink, blue and purple, and they have a scent.

Sweet pea extract is obtained by soaking the entire plant or at least one of its flower, stem, leaf, root and seed in a solvent at normal temperature or heated temperature, or by using an extractor such as a Soxhlet extractor. The extracted components may also be refined using a chromatography, etc. To obtain an extract offering an excellent effect of preventing or slowing aging, it is preferable to extract from the flower and stem, or especially from the flower. It is possible to extract from the entire flower including the petals, sepals, stamens and pistils, or only the petals may be selectively collected and extract taken from the petals alone. Sweet pea extract can be used as a dry powder or paste obtained by drying or freeze-drying any one of various solvent extracts or their diluents, concentrates or extracts.

An extraction solvent used to obtain sweet pea extract may be a polar solvent or nonpolar solvent. Examples include: water; alcohols such as methanol, ethanol, propanol and butanol; polyhydric alcohols such as propylene glycol and butylene glycol; ketones such as acetone and methyl ethyl ketone; esters such as methyl acetate and ethyl acetate; chain and poly ethers such as tetrahydrofuran and diethyl ether; polyethers such as polyethylene glycol; halogenated hydrocarbons such as dichloromethane, chloroform and tetrachloromethane; hydrocarbons such as hexane, cyclohexane and petroleum ether; aromatic hydrocarbons such as benzene and toluene; and pyridines. These substances may be used alone or two or more may be combined. Among the aforementioned extraction solvents, water or water-soluble organic solvents are preferred in obtaining an extract offering an excellent effect of elastase activity inhibition or cell growth promotion. Examples of water-soluble organic solvents include methanol, ethanol, propanol, 2-propanol, propylene glycol, butylene glycol and acetone, among others.

The blending ratio of sweet pea extract is not specified, but a range of approx. 0.0001 to 10 percent by dry weight is appropriate.

The cosmetic material, cell growth promoting agent, elastase activity inhibiting agent, anti-aging agent, or cosmetic material containing any of the foregoing, as proposed by the present invention, may contain vegetable oil and other oils, higher fatty acids, higher alcohols, silicones, anionic surface active agents, cationic surface active agents, amphoteric surface active agents, nonionic surface active agents, preservatives, sugars, metallic ion sealing agents, water-soluble polymers and other polymers, thickening agents, powder components, UV absorbents, UV blockers, hyaluronic acid and other moisture-keeping agents, aromatic agents, pH adjusters, and drying agents, among others. Other possible ingredients include vitamins, skin activation agents, blood-circulation promoting agents, normal-bacteria controlling agents, active enzyme erasers, anti-inflammatory agents, anticancer agents, whitening agents, sterilizers and other medicinal components or bioactive components.

Examples of oils include, among others, camellia oil, evening primrose oil, *macadamia* nut oil, olive oil, rape seed oil, corn oil, sesame oil, jojoba oil, germ oil, wheat germ oil, glycerin trioctanoate and other liquid oils; cacao oil, coconut oil, hardened coconut oil, palm oil, palm kernel oil, haze wax, haze kernel oil, hardened oil, hardened castor oil and other solid oils; and honey wax, candelilla wax, cotton wax, rice bran wax, lanolin, lanolin acetate, liquid lanolin, sugarcane wax and other waxes.

Examples of hydrocarbons include, among others, liquid paraffin, squalene, squalane, and microcrystalline wax.

Examples of higher fatty acids include, among others, lauric acid, myristic acid, palmitic acid, stearic acid, oleic acid, linoleic acid, linolenic acid, docosa-hexaenoic acid (DHA), and eicosapentaenoic acid (EPA).

Examples of higher alcohols include, among others, lauryl alcohol, stearyl alcohol, cetyl alcohol, cetostearyl alcohol and other linear alcohols; and monostearyl glycerin ether, lanolin alcohol, cholesterol, phytosterol, octyl dodecanol and other branched alcohols.

Examples of silicones include, among others, chain polysiloxanes such as dimethyl polysiloxane and methyl phenyl polysiloxane; and cyclic polysiloxanes such as decamethyl cyclopentane siloxane.

Examples of anionic surface active agents include, among others, sodium laurate and other fatty acid salts; sodium lauryl sulfate and other higher alkyl sulfate ester salts; POE triethanol amine lauryl sulfate and other alkyl ether sulfate ester salts; N-acyl sarcosinate, sulfosuccinic salt, and N-acyl amino acid salt.

Examples of cationic surface active agents include, among others, stearyl trimethyl ammonium chloride and other alkyl trimethyl ammonium salts; benzalkonium chloride, and benzethonium chloride.

Examples of amphoteric surface active agents include, among others, alkyl betaine, amide betaine and other betaine surface active agents.

Examples of nonionic surface active agents include, among others, sorbitan monooleate and other sorbitan fatty acid esters; and hardened castor oil derivatives.

Examples of preservatives include, among others, methyl paraben and ethyl paraben. Examples of metallic ion sealants include, among others, ethylene diamine disodium tetraacetate, edetic acid, sodium edetate and other edetates.

Examples of polymers include, among others, gum arabic, tragacanth gum, galactan, guar gum, carageenan, pectin, agar, quince seed, dextran, pullulan, carboxymethyl starch, collagen, casein, gelatin methyl cellulose, methyl hydroxypropypl cellulose, hydroxyethyl cellulose, sodium carboxymethyl cellulose (CMC), and sodium arginate.

Examples of thickening agents include, among others, carageenan, tragacanth gum, quince seed, casein, dextrin, gelatin, CMC, hydroxyethyl cellulose, hydroxypropyl cellulose, guar gum, xanthan gum and bentonite.

Examples of powder components include, among others, talc, kaolin, mica, silica, zeolite, polyethylene powder, polystyrene powder, cellulose powder, inorganic white pigment, inorganic red pigment, titanium-oxide coated mica, titanium-oxide coated talc, colored titanium-oxide coated mica and other pearl pigments, red 201, red 202 and other inorganic pigments.

Examples of UV absorbents include, among others, para-aminobenzoic acid, phenyl salicylate, para-methoxy isopropyl cinnamate, para-methoxy octyl cinnamate, and 2,4-dihydroxy benzophenone.

Examples of UV blockers include, among others, titanium oxide, talc, carmine, bentonite, kaolin, and zinc oxide.

Examples of moisture-keeping agents include, among others, polyethylene glycol, propylene glycol, dipropylene glycol, 1,3-butylene glycol, 1,2-pentane diol, glycerin, diglycerin, polyglycerin, xylitol, maltitol, maltose, sorbitol, glucose, fructose, chondroitin sodium sulfate, sodium hyaluronate, sodium lactate, pyridonecarboxylic acid, and cyclodextrin.

Examples of medicinal components include, among others, vitamins such as vitamin A oil, retinol and other vitamin As; riboflavin and other vitamin B2s; pyridoxine hydrochloride and other vitamin B6s; L-ascorbic acid, L-ascorbic acid phosphate ester, L-ascorbic acid ester monopalmitate, L-ascorbic acid ester dipalmitate, L-ascorbic acid-2-glucoside and other vitamin Cs; calcium pantothenate and other pantothenates; vimtain D2, cholecalciferol and other vitamin Ds; α-tocopherol, tocopherol acetate, nicotinic acid DL-α-tocopherol and other vitamin Es.

In addition to the above, components that should desirably coexist in the formulation include glutathione, saxifraga stolonifera extract and other whitening agents; royal jelly, beech extract and other skin activation agents; capsaicin, zingherone, cantharides tincture, ichthammol, caffeine, tannic acid, γ-oryzanol and other blood-circulation promoting agents; glycyrrhizic acid derivative, glycyrrhetinic acid derivative, azulene and other anti-inflammatory agents; arginine, serine, leucine, tryptophane and other amino acids; and normal-bacteria controlling agents such as maltose sucrose condensation product and lysozyme chloride.

Other favorable ingredients include various extracts such as chamomile extract, parsley extract, beech extract, wine yeast extract, grapefruit extract, woodbine extract, rice extract, grape extract, hop extract, rice bran extract, loquat extract, *coix* seed extract, *swertia japonica* extract, melilot extract, birch extract, licorice extract, peony extract, soapwort extract, sponge gourd extract, chili pepper extract, lemon extract, gentian root extract, *perilla* extract, aloe extract, rosemary extract, sage extract, thyme extract, seaweed extract, cucumber extract, carrot extract, horse chestnut extract, hamamelis extract, and mulberry extract.

The cosmetic material, cell growth promoting agent, elastase activity inhibiting agent, anti-aging agent, or cosmetic material containing any of the foregoing, as proposed by the present invention, may be applied in the form of aqueous solution, oil, milk, suspension or other liquid; gel, cream or other semi-solid; or powder, granule, capsule, microcapsule, solid or other solid. Preparation into any of these forms can be done using any known conventional method, to create a lotion, milk, gel, cream, ointment, plaster, poultice, aerosol, powder, granule and various other types of dosage forms. They can be attached, pasted, sprayed or otherwise applied onto the body.

Specific purposes of use of the aforementioned cosmetic material, cell growth promoting agent, elastase activity inhibiting agent, anti-aging agent, or cosmetic material containing any of the foregoing, include a skin lotion, milk, cream, pack and other skin care products; makeup base lotion, makeup cream, milky or cream or paste foundation, lipstick, eye color, cheek color and other makeup products; hand cream, leg cream, body lotion and other body care products; bath products; and hair care products.

The present invention is explained in further details below using examples. It should be noted, however, that the present invention is not at all limited to these examples.

[Extract 1]

45.9 g of sweet pea petals (purple) and 459 g of distilled water were placed in a bottle and heated for 30 minutes in a hot water bath of 90 to 100° C. After cooling, the mixture was wrung in a sheet of gauzes and separated further for 10 minutes in a centrifugal separator operated at 3,000 rpm. The supernatant was condensed in a rotary evaporator adjusted to a hot water bath temperature of 65° C., after which water was added to a weight of 45.9 g. The soluble solid content of the extract was 4.87%.

[Extract 2]

Extract 1 was condensed in a rotary evaporator to obtain a ×5 concentrate. The soluble solid content was 24.4%.

[Extract 3]

148.2 g of sweet pea stem and 741 g of distilled water were placed in a bottle and heated for 60 minutes in a hot water bath of 90 to 100° C. After cooling, the mixture was wrung in a sheet of gauzes and separated further for 10 minutes in a centrifugal separator operated at 3,000 rpm. The supernatant was condensed in a rotary evaporator adjusted to a hot water bath temperature of 65° C., after which water was added to a weight of 29.6 g. The soluble solid content of the extract was 13.6%.

[Elastase Activity Inhibition Test]

50 μl of each of Extracts 1 to 3 that has been diluted to each concentration, 50 μl of elastase (20 μg/ml), and 100 μl of 1 mM N-succinyl-Ala-Ala-Ala-p-nitroanilide were mixed and reacted for 50 minutes at 25° C., and light absorbance was measured at 415 nm. Dilution of each solution was done using a buffer solution constituted by 0.2 M tris-HCL buffer (pH 8.0). As a control, a specimen was prepared where the buffer solution was added instead of elastase. The inhibition rate was calculated using the formula below.

Inhibition rate (%) (1—(Light absorbance of specimen containing sample—Light absorbance of control specimen containing sample)/(Light absorbance of specimen not containing sample—Light absorbance of control specimen not containing sample))×100

The results are shown in FIG. 1.

As the results show, Extract 1 demonstrated elastase activity inhibition effects of 29% and 6% at added concentrations of 5.0% and 2.5%, respectively. The elastase activity inhibition effect of Extract 2 was 44% at an added concentration of 2.5%. When Extract 2 was measured at an added concentration of 5.0%, the light absorbance of the material itself was high and an accurate value could not be obtained. Therefore, the measured result was excluded. On the other hand, Extract 3 did not show elastase activity inhibition effect.

[Cell Growth Promotion Test]

In a DMEM culture medium containing 10% FBS (fetal bovine serum), normal human fibroblasts were inoculated onto a 96-well plate at a concentration of $1\times10^4$ cells/well. One day after the inoculation, the culture medium was changed to a DMEM culture medium containing 1% FBS where the sample was added and the cells were cultured for six days, after which the cell mass was obtained using the MTT assay method. A specimen to which no sample was added was used as a control. From the light absorbance obtained, the change in cell mass was calculated using the formula below. FBS was used as a positive control.

Change in cell mass (%)=Light absorbance of specimen containing sample/Light absorbance of control specimen×100

The results are shown in FIG. 2.

As the results show, the cell mass increased to 180% after 2.5% of Extract 2 was added. The change in cell mass after addition of 2.5% of positive control FBS (fetal bovine serum) was 134%, indicating that Extract 2 has better cell growth effect than FBS.

When 2.5% of Extract 1 was added, the cell mass increased to 120%. When 2.5% of Extract 3 was added, the cell mass increased to 127%. Accordingly, both extracts have excellent cell growth effect although not as good as FBS.

[Cell Toxicity Tests]

1. Cell Toxicity Test Using Fibroblasts

Normal human fibroblasts (NHFB) were inoculated onto a 96-well plate at $3.5\times10^4$ cells/ml, and cultured for five days in a 5% $CO_2$ environment of 37° C. in temperature. In a condition of confluent, the culture medium was changed to a DMEM culture medium containing 10% serum and one of Extracts 1 to 3 whose content has been adjusted to 0.008% to 1.0%, to expose the cells to the extract. After 24 hours of exposure, the cell survival rate was obtained using the MTT assay method. The results are shown in FIG. 3. None of Extracts 1 to 3 exhibited toxicity with respect to normal human fibroblasts at concentrations up to 1.0%.

2. Method of Toxicity Test Using Human Keratinized Cells

Normal human keratinized cells (NHKC) were inoculated onto a 96-well plate at $4.0\times10^5$ cells/ml, and cultured for one day in a 5% $CO_2$ environment of 37° C. in temperature. In a condition of confluent, the culture medium was changed to a non-serum culture medium for growing keratinized cells, containing one of Extracts 1 to 3 whose content has been adjusted to 0.008% to 1.0%, to expose the cells to the extract. After 24 hours of exposure, the cell survival rate was obtained using the MTT assay method. The results are shown in FIG. 4. None of Extracts 1 to 3 exhibited toxicity with respect to normal human keratinized cells at concentrations up to 1.0%.

3. Method of Toxicity Test Using Cells Derived from Ocular Mucous Membrane

A cell strain derived from rabbit cornea (SIRC) was inoculated onto a 96-well plate at $4.0 \times 10^5$ cells/ml, and cultured for five days in a 5% $CO_2$ environment of 37° C. in temperature. In a condition of confluent, the culture medium was changed to a MEM culture medium containing 10% serum and one of Extracts 1 to 3 whose content has been adjusted to 0.008% to 1.0%, to expose the cells to the extract. After 24 hours of exposure, the cell survival rate was obtained using the MTT assay method. The results are shown in FIG. 5. None of Extracts 1 to 3 exhibited toxicity with respect to cell strains derived from rabbit cornea at concentrations up to 1.0%.

Based on the toxicity test results shown above, Extracts 1 to 3 exhibited no toxicity at concentrations up to 1.0% with respect to normal human fibroblasts, normal human keratinized cells or cell strains derived from rabbit cornea. This confirms that the sweet pea extract proposed by the present invention is very safe.

[Test of Aging Prevention/Slowing Effect]

Ten female subjects (35 to 55 years of age) complaining rough skin, fine lines, dry skin, etc., were asked to apply specimens prepared according to the recipes explained below, twice a day (morning, evening) for consecutive four weeks, and the effects were evaluated after four weeks. To check the effects of preventing or slowing aging, the test results were evaluated in the areas of hydration, smoothness and elasticity of skin. Table 1 shows the numbers of subjects indicating that the skin was felt hydrated, smoother and firmer, and those indicating that no effect was felt.

TABLE 1

|  | Hydration of skin The skin became hydrated. | Smoothness of skin The skin became smoother. | Elasticity of skin The skin became firmer. |
| --- | --- | --- | --- |
| Number of subjects feeling the effect | 10 | 8 | 9 |
| Number of subjects not feeling any effect | 0 | 2 | 1 |

Examples of recipes conforming to the present invention are explained below. It should be noted, however, that the present invention is not at all limited to these examples.

EXAMPLE 1

<Skin milk>

|  |  | Mass % |
| --- | --- | --- |
| (A) | Purified water | Remainder |
|  | 1,3-butylene glycol | 6.0 |
|  | 1,2-pentane diol | 2.0 |
|  | Carboxyvinyl polymer | 0.12 |
|  | Glycerin | 3.0 |
|  | Betaine | 3.0 |
|  | Glucose | 3.0 |
| (B) | Jojoba oil | 1.5 |
|  | Squalane | 1.5 |
|  | Polyoxy-ethylene hardened caster oil | 1.0 |

-continued

<Skin milk>

|  |  | Mass % |
| --- | --- | --- |
| (C) | Extract 1 | 1.0 |
|  | Potassium hydroxide | 0.05 |

[Formula] The water-phase ingredients in A and oil-phase ingredients in B were heated and dissolved, respectively, after which the oil-phase ingredients were mixed with the water-phase ingredients and emulsified using an emulsifier. After the mixture was cooled, the ingredients in C were mixed to obtain a skin milk.

EXAMPLE 2

<Skin lotion>

|  |  | Mass % |
| --- | --- | --- |
| (A) | Purified water | Remainder |
|  | 1,3-butylene glycol | 7.0 |
|  | 1,2-pentane diol | 1.5 |
|  | Glycerin | 1.5 |
|  | Betaine | 0.5 |
|  | Glucose | 1.0 |
|  | Extract 2 | 0.1 |
|  | Rosemary extract | 0.3 |

[Formula] The above ingredients were mixed and dissolved to obtain a skin lotion.

EXAMPLE 3

<Beauty essence>

|  |  | Mass % |
| --- | --- | --- |
| (A) | Purified water | Remainder |
|  | 1,3-butylene glycol | 6.0 |
|  | 1,2-pentane diol | 2.0 |
|  | Betaine | 2.0 |
|  | Glucose | 1.0 |
|  | Glycerin | 5.0 |
|  | Carboxyvinyl polymer | 0.15 |
| (B) | Potassium hydroxide | 0.04 |
|  | Sodium hyaluronate (1% aqueous solution) | 0.5 |
|  | Extract 1 | 0.5 |

[Formula] After the ingredients in A above were mixed and dissolved, the ingredients in B were mixed to obtain a beauty essence.

EXAMPLE 4

<Cream>

|  |  | Mass % |
| --- | --- | --- |
| (A) | Purified water | Remainder |
|  | Dipropylene glycol | 10.0 |
|  | Carboxyvinyl polymer | 0.12 |
|  | Glycerin | 3.0 |
|  | Betaine | 3.0 |
|  | Glucose | 3.0 |

-continued

<Cream>

| | | Mass % |
|---|---|---|
| (B) | Jojoba oil | 8.5 |
| | Squalane | 10.0 |
| | New oil-type glycerin monostearate | 3.0 |
| | Sorbitan monostearate | 1.5 |
| | Polyoxy monostearate Ethylene sorbitan (20 E.O.) | 1.0 |
| (C) | Extract 2 | 0.1 |
| | Potassium hydroxide | 0.05 |

[Formula] The water-phase ingredients in A and oil-phase ingredients in B were heated and dissolved, respectively, after which the oil-phase ingredients were mixed with the water-phase ingredients and emulsified using an emulsifier. After the mixture was cooled, the ingredients in C were mixed to obtain a cream.

EXAMPLE 5

<Skin milk>

| | | Mass % |
|---|---|---|
| (A) | Purified water | Remainder |
| | 1,3-butylene glycol | 5.0 |
| | 1,2-pentane diol | 0.5 |
| | Carboxyvinyl polymer | 0.12 |
| | Glycerin | 2.0 |
| | Betaine | 3.0 |
| | Glucose | 3.0 |
| (B) | Macadamia nut oil | 1.0 |
| | Squalane | 2.0 |
| | Polyoxy-ethylene hardened caster oil | 1.0 |
| (C) | Extract 3 | 1.0 |
| | Potassium hydroxide | 0.05 |

[Formula] The water-phase ingredients in A and oil-phase ingredients in B were heated and dissolved, respectively, after which the oil-phase ingredients were mixed with the water-phase ingredients and emulsified using an emulsifier. After the mixture was cooled, the ingredients in C were mixed to obtain a skin milk.

The invention claimed is:

1. A method for improving rough skin, fine lines, and/or dry skin of a subject, comprising administrating a cosmetic material comprising a sweet pea extract to the subject in an amount of the sweet pea extract effective to improve rough skin, fine lines, and/or dry skin of the subject, said sweet pea extract being an extract from the flower of sweet pea using water or a water-soluble organic solvent and having activity of elastase activity inhibition and cell growth promotion, wherein the cosmetic material comprises the sweet pea extract in an amount of 0.001 to 10% by dry weight.

2. The method according to claim 1, wherein the cosmetic material is prepared in topical form, and the administrating step comprises applying the cosmetic material on the rough skin, fine lines, and/or dry skin to be improved.

3. The method according to claim 1, wherein the cosmetic material includes a plant extract or plant extracts, wherein all of the plant extract(s) included in the cosmetic material is/are the sweet pea extract.

4. The method according to claim 1, wherein the cosmetic material includes a plant extract or plant extracts, wherein all of the plant extract(s) included in the cosmetic material is/are the sweet pea extract and at least one selected from the group consisting of a saxifrage stolonifera extract, beech extract, chamomile extract, parsley extract, beech extract, wine yeast extract, grapefruit extract, woodbine extract, rice extract, grape extract, hop extract, rice bran extract, loquat extract, coix seed extract, swertia japonica extract, melilot extract, birch extract, licorice extract, peony extract, soapwort extract, sponge gourd extract, chili pepper extract, lemon extract, gentian root extract, perilla extract, aloe extract, rosemary extract, sage extract, thyme extract, seaweed extract, cucumber extract, carrot extract, horse chestnut extract, hamamelis extract, and mulberry extract.

* * * * *